United States Patent [19]

Müller-Ruchholtz et al.

[11] Patent Number: 4,738,773
[45] Date of Patent: Apr. 19, 1988

[54] SEPARATOR FOR MAGNETIC PARTICLES FROM LIQUID PHASE

[75] Inventors: Wolfgang Müller-Ruchholtz, Molfsee; Jörg Kandzia, Kirchzarten-Bruckmühle; Wolfgang Haas, Reichenhall; Gabriele Leyhausen, Kiel, all of Fed. Rep. of Germany

[73] Assignee: Bayer Aktiengesellschaft, Leverkusen, Fed. Rep. of Germany

[21] Appl. No.: 868,823

[22] Filed: May 29, 1986

[30] Foreign Application Priority Data

Jun. 22, 1985 [DE] Fed. Rep. of Germany ....... 3522365

[51] Int. Cl.$^4$ .............................................. B03C 1/02
[52] U.S. Cl. .................................. 209/214; 209/213; 209/223.1; 209/232; 210/695; 210/222
[58] Field of Search ........................................ 209/1–4, 209/8, 39, 213–215, 223.1, 232, 636; 210/222, 223, 695

[56] References Cited

U.S. PATENT DOCUMENTS

| | | | |
|---|---|---|---|
| 3,006,472 | 10/1961 | Clute | 209/214 |
| 3,140,714 | 7/1964 | Murphy, Jr. et al. | 209/2 U X |
| 3,451,545 | 6/1969 | Studer | 209/8 |
| 3,470,067 | 9/1969 | Warren et al. | 209/8 |
| 4,066,536 | 1/1978 | Ball et al. | 209/1 X |
| 4,085,039 | 4/1978 | Allen | 209/227 X |
| 4,187,170 | 2/1980 | Westcott et al. | 209/8 X |
| 4,219,411 | 8/1980 | Yen et al. | 209/213 |
| 4,343,707 | 8/1982 | Lucas | 210/695 |

FOREIGN PATENT DOCUMENTS 3444939 6/1986 Fed. Rep. of Germany.

Primary Examiner—Robert B. Reeves
Assistant Examiner—Edward M. Wacyra
Attorney, Agent, or Firm—Sprung Horn Kramer & Woods

[57] ABSTRACT

A separator for the magnetic removal of magnetizable particles, consists of an application unit for the application and the transport of sample and buffer, a separating unit of plastic or glass for the removal of the magnetizable particles, and a collecting unit. The separating unit is provided with one or more electromagnets, which are able, owing to their magnetic force, to hold the magnetizable particles back in the separating unit.

12 Claims, 2 Drawing Sheets

SEPARATOR FOR MAGNETIC PARTICLES FROM LIQUID PHASE

BACKGROUND OF THE INVENTION

The invention relates to a separator to remove magnetic particles from liquid phases, consisting of an application unit, a separating unit and a collecting unit. This separator can be used to fractionate biological materials, in particular to remove cells, antigens, antibodies, enzymes etc., with the aid of magnetic microspheres (MIMS).

There has been a considerable increase in recent years in the interest in efficient analytical and preparative cell separation procedures. Since cell biologists have increasingly turned their attention to the investigation of the functional interaction of even the smallest subpopulations of cells within heterogeneous mixtures, the requirements of a separation technique are not only the necessary quantitative physical efficiency but also the ability to make specific qualitative differentiations. Up to the present time, the density centrifugation technique, which separates various cells on the basis of the physical parameters volume and density, has retained its uncontested value for the first requirement mentioned (see Hutchins, D. and C. M. Steel, in: Peters, H. editor: Separation of cells and subcellular elements 1979; A. J. Fluks, 1981, J. Immunol. Methods 41: 225; A. J. Ulmer and Flad H. D., 1984, Immunobiol. 166: 238), but at the expense of limited specificity (selectivity).

The only techniques which can be used for the second requirement are those which, owing to their ability to make use of different molecular surface structures of various cells (target molecules such as antigens, receptors or the like) as separation parameters, carry out biospecific, and thus selective, separations. In this connection, solid-phase affinity techniques, which separate on the basis of serological reactions, should be especially picked out.

These methods allow specific separation of cells or cellular material by differentiation of molecular surface structures, for example antigens, by immobilization of antibodies on plastic surfaces (for example the panning procedure: Wysocki, L. J. and V. L. Sato, 1978, Proc. Nat'l. Acad. Sci. 75: 2844; Basch, R. S. et al., 1983, J. Immunol. Methods 56: 269), glass or gel materials (Basch, R. S. et al., loc. cit.) which can be packed to form columns. The disadvantages of these procedures are non-specific binding reactions with material surfaces, the blockage of columns owing to aggregating particles or cells, adverse effects on sensitive cells owing to shear forces, long process times and, very especially, the lack of capacity to deal with large amounts.

In contrast, in liquid-phase procedures, in which the actual separation process takes place from dilute suspensions, it is possible almost entirely to eliminate nonspecific adhesion, inadequate conservation of cells, and shear forces. The following may be mentioned in this connection: Cell immunoelectrophoresis (van Oss et al., 1979, Immunol. Communic. 8: 419), FACS (Loken, M. R. and A. M. Stall, 1982, J. Immunol. Methods 50: R 85), and magnetic cell separation techniques based on antibody-conjugated magnetic microspheres (MIMS). Common to all these techniques is the combination of the serological specificity of antibodies with a controllable physical force: electric field, optical recognition or magnetic field.

Although, for example, FACS at present represents the state of the art in the field of analysis—despite its high costs of acquisition and maintenance, in particular because of its multifactorial character—it has an important disadvantage, as has also cell immunoelectrophoresis: the capcity available for preparative use is strictly limited and is inadequate to deal with large amount of cells in an acceptable time.

In contrast, the use of magnetic microspheres offers remarkable advantages, since magnetic separation procedures with microspheres are low-cost and straightforward in their process sequence and, in particular, can be used preparatively with acceptable economy not only for dealing with large amounts of cells ($10^6$–$10^{12}$ cells) but also for the rapid isolation of other cellular particles.

However, in this connection, an additional important system objective must be the parallel development and provision of a favourable priced unit of apparatus, in which the specific separating efficiency of MIMS is exploited, in an industrially reliable and reproducible manner, and the extensive analytical and preparative possibilities are made use of flexibly and quantitatively efficiently. The present invention relates to the provision of a separator of this type.

SUMMARY OF THE INVENTION

The invention relates to a separator for the magnetic removal of particles. These are, in particular, biological particles, especially cells, but also molecular structures such as, for example, enzymes, antigens, antibodies or other biological substances which (a) have previously been biochemically bound, by affinity or otherwise, to a magnetizable component such as, for example, magnetic microspheres, (b) have subjected a magnetizable component to secondary uptake, or (c) naturally contain a molecular structure which is susceptible to magnetic influence. This removal takes place from the liquid phase in a continuous flow system. This entails those particles which contain the magnetizable component bound according to (a), taken up according to (b), or contained according to (c), being held fixed in the magnetic field (positive selection) while, at the same time, all the other particles pass through with the liquid flow and are collected (negative selection).

DETAILED DESCRIPTION OF THE DRAWINGS

Figure 1:
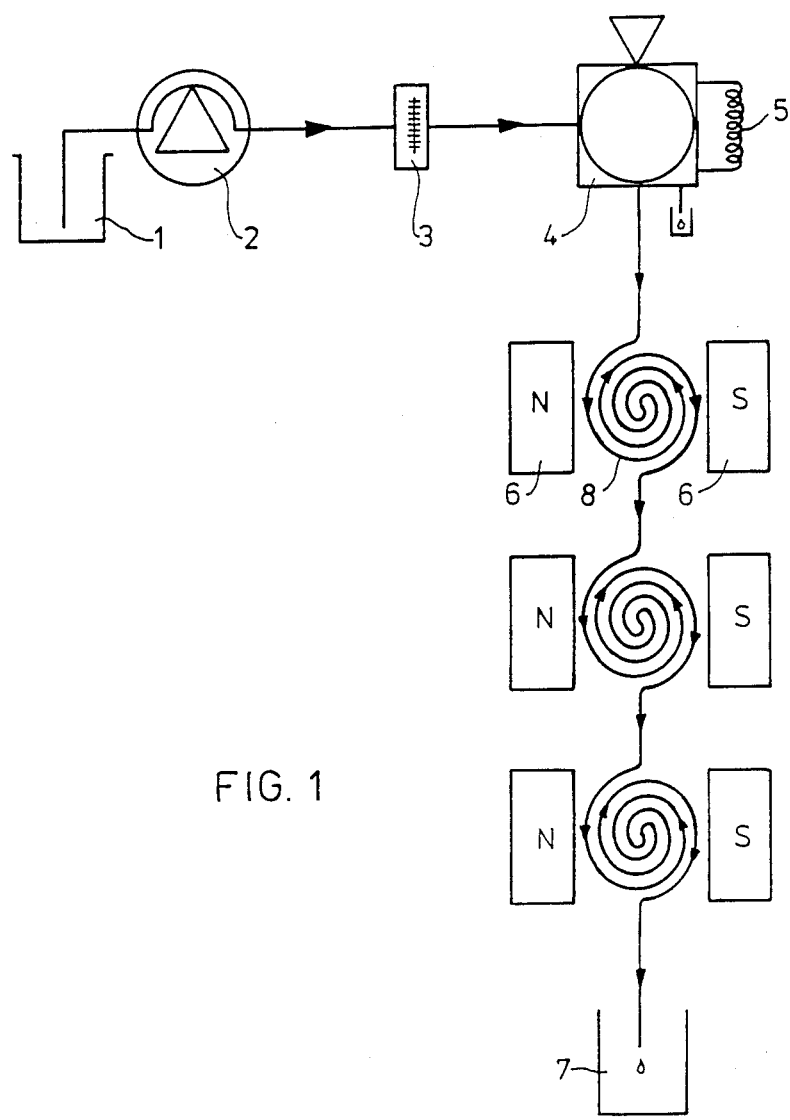
FIG. 1 is a schematic of a separator according to the invention.

As FIG. 1 shows, the invention relates to a separator for the magnetic removal of mganetizable particles, whose application unit consists of a rheodyne valve system (4) with a sample loop (5), a peristaltic pump (2) and a compact flowmeter (3), or consists of the combination of several of these individual elements. The application unit is designed for input of sample volumes of 1 $\mu$l–1000 ml, in particular 100 $\mu$l to 10 ml, volume of the sample loop. The sample-loading valve (4) is a multiway valve and consists of a magnetic material, and the sample loop (5) likewise consists of a magnetic material, for example special steel or Teflon tubing. The sample loop is positioned so that, after sample loading, the entire sample is introduced, by means of upstream pump unit (2), into the separating unit. At the same time, a pump, such as, for example, peristaltic pump (2), removes, from an upstream reservoir (1), reservoir buffer, rinsing buffer or the like, which is pumped through the separating unit by means of the pump, either directly or via the sample loop depending on the position of the loading valve. The peristaltic pump produces infinitely variable flow rates which can be measured and monitored by means of the incorporated compact flowmeter (3).

The choice of the flow rate depends on the total volume of the separating unit, the volume of the sample and, in general, on the physical and chemical nature of the sample, such as, for example, the particle count and the viscosity. Flow rates of 0.2–20 ml/min, in particular 0.4–4 ml/min, normally 0.4–1 ml/min, have proved suitable.

The invention also relates to a separator for the magnetic removal of magnetizable particles, whose separating unit consists, quite generally, of specially shaped chambers (8), of an extremely wide variety of sizes and volumes, of glass, with and without coating (for example silicone), or of plastics, in particular Teflon and its derivatives. Various embodiments of the separating unit are shown in FIGS. 2–7.

This separating unit consists of one or more elements (1–20, advantageously 1–6, in particular 3, elements) which, in toto, are fabricated from one or more individual pieces, preferably from Teflon tubing of length 1–200 cm, in particular 1–30 cm, with different diameters (0.1–6 mm, in particular 0.1–2 mm), and can be assembled in a variable number in a coupler system.

Figures 2, 3, 4, 5, 6, 7:
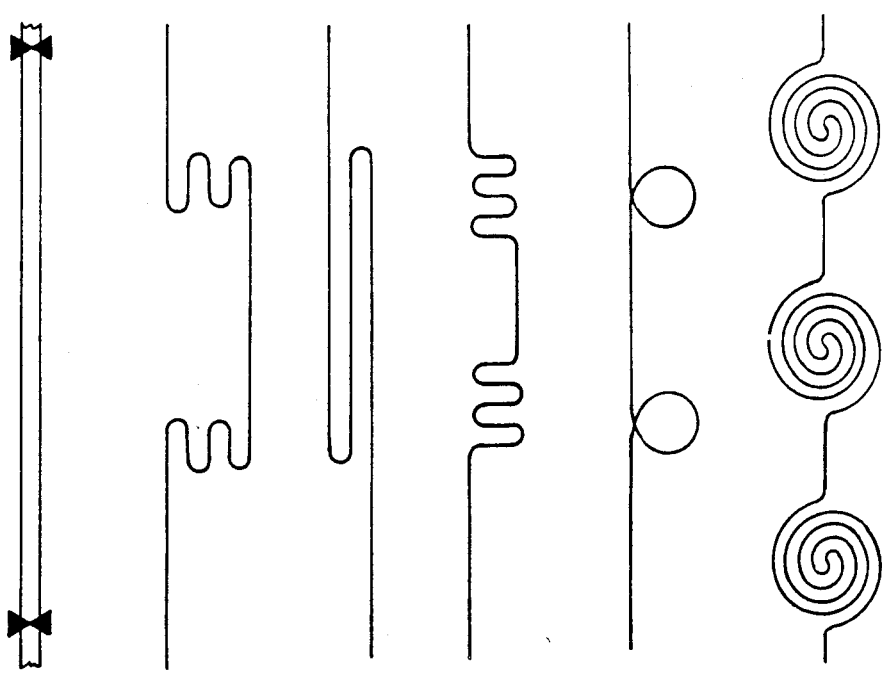
FIGS. 2 to 7 are different embodiments of the separating unit shown in FIG. 1.

The "separating helix" of Teflon tubing shown in FIG. 7 is preferred. It is mechanically and chemically inert, can be shaped and has, at the same time, intrinsic stability, and can be autoclaved and sterilized. It is designed so that it permits optimum positioning in the magnetic field with a maximum surface area facing the magnetic field and, at the same time, minimalization of the total volume (avoidance of extensive dilution effects). It is would circularly and thus has a form without edges and kinks, which would result in retention of particles and thus in system losses. Thus, it is designed so that abrupt changes in calibre are avoided in order to ensure a steady, non-turbulent "flux". Its form is such that no adhesion of particles can take place. It is amenable to extension and development in the sense of a general design principle.

A possible variation of the separating unit is its construction of one or more separating chambers which are connected together. These separating chambers consist of glass or plastic, in particular Teflon, and are held together aand sealed by an amagnetic metal frame. They are mechanically and chemically inert, intrinsically stable, sterilizable and autoclavable. They are designed so that they permit optimum positioning in the magnetic field, with a maximum surface area facing the magnetic field and, at the same time, minimalization of the total volume.

An essential part of the separating unit are the electromagnets (6) which, in a preferred embodiment, are infinitely variable.

When several magnets are used, it is advantageous to supply current to, and to control, each by itself via a separate power supply unit.

The field strengths which can be achieved cover a range of 0,1 to 40 kilo-Gauss. The actual field strength for each magnet is, by means of a Hall probe installed in the field, directly read off, checked and, where appropriate, recorded.

The power supply units are operated with alternating current, the power supply unit delivering a stabilized direct current or alternating current, which is characterized as continuous or pulsed current. The pulsed current has a variable frequency, amplitude and pause time and a sinusoidal, but preferably rectangular or sawtoothed, form which can be checked and recorded oscillographically. The output of the power supply units which are used depends on the desired field strength, the latter being determined by the experimental arrangement.

The number of electromagnets depends essentially on the type and shape of the separating unit, and is 1 to 20, 2 to 6 being preferred. 3 electromagnets are particular preferred.

Figure 8:
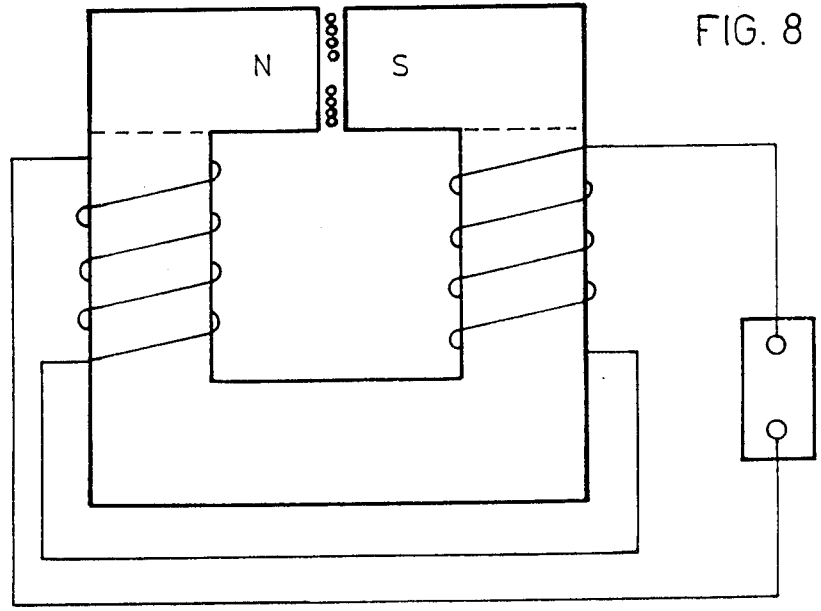
FIG. 8 shows the details of the electromagnets of FIG. 1.

The electromagnets which are used are composed of coils, through which current passes, of any shape, with a core of soft iron, ferrite or other ferro/paramagnetic substances (FIG. 8 shows a detailed representation). The actual magnetic field acting on the separating unit depends on the size of the air gap between the north and south poles, that is to say on the length and density of the lines of field running between them. Depending on the power supply unit used, intermittent or constant, homogeneous magnetic fields act on the separating unit which is located in this air gap.

A component of the separator is a collecting unit, which consists of a fraction collector (7), it being possible to set and control the fraction volume via an optical recognition unit (photometer, drop-counter).

All the controllable functions can be automatically controlled by means of microprocessors. This applies to individual functions as well as to several connected together. This results in, for example, the options of continuous automatic sample loading, buffer changing and optical/electronic checks with single to multiple valvecontrolled feedback.

Use example

1:1 mixtures of peripheral blood lymphocytes from HLA-distinct donors (HLA-Bw6+ and HLA-Bw4+) are incubated with MIMS. A monolonal anti-HLA Bw6 antibody is affinity-bound to the MIMS, that is to say they act as magnetic separating reagent. The MIMS are prepared, and the lymphocytes are obtained, as described in corresponding U.S. application Ser. No. 806,056, filed Dec. 5, 1986.

A sample comprising 2 ml ($1-10\times 10^6$ cells+0.5–2.5 mg of MIMS) is introduced, via a rheodyne valve, into the sample loop which is connected to the upper ends of the separating helix. Then three consecutive electromagnets are switched on. The upper part of the separating helix is exposed to a magnetic field of 1.7 kilo-Gauss (KG), the middle part is exposed to a magnetic field of 3.4 KG and the lower part is exposed to a magnetic field of 5.7 KG.

The cell suspension is now eluted, by means of a peristaltic pump in a continuous "free-flow" system with a flow rate of 0.4 ml/min, through the separating helix and is thus exposed to the magnetic fields.

The liquid collected as eluate fraction has twice the volume of the separating helix. The electromagnets are then switched off, and the magnetic fraction is obtained by pulsatile flushing by means of the pump.

The separating efficiency of this overall system is composed of the biological specificity of the antibody molecule used here, of the physical effect of the magnetic field, which should be selected to accord with the experimental conditions, and the material, shape and volume of the separating column.

Using the separator described here, the following data relating to the use example were obtained with only one run:

The purity of the eluate fraction is between 96 and 100%, which means that the magnetic fields are strong enough to hold back the magnetic particles together with the cells bound thereon.

The purity of the magnetic fraction is 85 to 95%, that is to say 5 to 15% of the cells are held back non-specifically. The recovery of the cells is between 95 and 100%. The fact that the vitality of the cells after the separation was hardly impaired, still being between 92 and 99%, shows that the magnetic fields were set at an optimum for this experiment.

In summary, it may be stated that the separator can be used for analysis and preparation.

What is claimed is:

1. A separator for the magnetic removal of magnetizable particles, comprising: application means for applying and transporting a sample of magnetizable particles in a liquid phase, separating means receptive of the transported sample for removing the magnetizable particles and comprising means forming a free flowing flow path extending downwardly from the application means and including at least one helical separating member in the flow path and at least one electromagnet adjacent said at least one helical separating member with sufficient magnetic force to hold the magnetizable particles back in the separating member and collecting means for receiving the liquid phase of the sample with the magnetizable particles removed.

2. The separator according to claim 1, wherein said application means comprises a sample loop, a multiway valve, a pump and a flowmeter.

3. The separator according to claim 2, wherein the sample loop has a volume of from 1 $\mu$l to 1000 ml.

4. The separator according to claim 1, wherein the separating member consists of one of glass and plastic, with or without a coating.

5. The separator according to claim 1 wherein the separating member is in the form of one of chambers, pieces of tubing, and tubes.

6. The separator according to claim 1 wherein said separating means consists of 1-20 separating members.

7. The separator according to claim 1 wherein each said at least one electromagnet is supplied with current via its own power supply unit.

8. The separator according to claim 7 wherein each said at least one electromagnet is infinitely variable by means of its power supply unit.

9. The separator according to claim 1, wherein the collecting means comprises a fraction collector.

10. Use of the separator according to claim 1 for the removal of magnetic particles.

11. Process for the removal of magnetic particles, wherein the separator according to claim 1 is used.

12. The separator according to claim 1, wherein the at least one helical separating member comprises tubing wound in an inwardly extending spiral and thereafter in an outwardly extending spiral.

* * * * *